United States Patent
Yang et al.

(10) Patent No.: US 9,642,839 B2
(45) Date of Patent: May 9, 2017

(54) SUBSTANCE HAVING TYROSINE KINASE INHIBITORY ACTIVITY AND PREPARATION METHOD AND USE THEREOF

(71) Applicant: Institute of Radiation Medicine, China Academy of Military Medical Sciences Pla, Beijing (CN)

(72) Inventors: Xiaoming Yang, Beijing (CN); Lin Wang, Beijing (CN); Changyan Li, Beijing (CN); Yiqun Zhan, Beijing (CN); Jing Liu, Beijing (CN); Teng Luo, Beijing (CN); Haiyan Yan, Beijing (CN); Shouguo Zhang, Beijing (CN); Wei Li, Beijing (CN); Xiaoxue Wen, Beijing (CN); Tao Peng, Beijing (CN); Lu Li, Beijing (CN)

(73) Assignee: Institute of Radiation Medicine, China Academy of Military Medical Sciences Pla (CN)

( * ) Notice: Subject to any disclaimer, the term of this patent is extended or adjusted under 35 U.S.C. 154(b) by 0 days.

(21) Appl. No.: 14/900,473

(22) PCT Filed: Jun. 20, 2013

(86) PCT No.: PCT/CN2013/000720
§ 371 (c)(1),
(2) Date: Dec. 21, 2015

(87) PCT Pub. No.: WO2014/201587
PCT Pub. Date: Dec. 24, 2014

(65) Prior Publication Data
US 2016/0151334 A1    Jun. 2, 2016

(51) Int. Cl.
*C07D 403/06* (2006.01)
*A61K 31/4178* (2006.01)
*C07D 209/34* (2006.01)
*A61K 31/4184* (2006.01)

(52) U.S. Cl.
CPC ...... *A61K 31/4178* (2013.01); *A61K 31/4184* (2013.01); *C07D 209/34* (2013.01); *C07D 403/06* (2013.01)

(58) Field of Classification Search
CPC .................................................. C07D 403/06
See application file for complete search history.

(56) References Cited

U.S. PATENT DOCUMENTS 7,148,249 B2  12/2006  Kley et al.
2004/0204407 A1  10/2004  Tang et al.

FOREIGN PATENT DOCUMENTS

WO  9807695 A1  2/1998
WO  03027102 A1  4/2003

OTHER PUBLICATIONS van Alphen, Recueil des Travaux Chimiques des Pays-Bas et de la Belgique, 1940, 59, pp. 289-297.*
Kim et al., Bioorganic & Medical Chemistry Letters, vol. 22, Issue 15, available online Jun. 16, 2012, pp. 4979-4985.*
Sassatelli. M. et al.. Synthesis and Antiproliferative Activities of Indolin-2-one Derivatives Bearing Amino Acid Moieties. European Journal of MEDICrNAL Chemistry, 2006. vol. 41. No. 6, pp. 709-716. ISSN: 0223-5234.
Chiang. C.C. ct al .. Discovery of Pyrrolc-Indoliu-2-oncs as Aurora Kinase Inhibitors with a Different InItibition Profile. Journal of Medicinal Chemistry, 2010. vol. 53. No. 16, pp. 5929-5941. LSSN: 0022-2623.
Miura. T. et al., Stereoselective Oxindolc Synthesis by Palladium-Catalyzed Cyclization Reaction of 2-(Alkynyl)aryl Isocyanates with Amidcs. Organic Letters. 2009. vol. II. No. 10.pp. 2141-2143. ISSN: 1523-7060.
International Search Report for Application No. PCT/CN2013/000720 dated Mar. 27, 2014.
International Preliminary Report on Patentability, Chapter I, for Application No. PCT/CN2013/000720 dated Dec. 22, 2015.
Extended European Search Report for Application # EP13887442.5 Dated Nov. 25, 2016.

* cited by examiner

*Primary Examiner* — Laura L Stockton
(74) *Attorney, Agent, or Firm* — Lerner, David, Littenberg, Krumholz & Mentlik, LLP

(57) ABSTRACT

Disclosed in the present disclosure are substances having tyrosine kinase inhibitory activity and a preparation method and use thereof, wherein the substances are the compounds having the structure of general formula (I) or the geometric isomers or pharmaceutical salts thereof. Through evaluation on tyrosine kinase inhibitory activity and related experiments, the present disclosure demonstrates that these compounds have a good tyrosine kinase inhibitory activity, and may inhibit a variety of tumor cells, and thus may be developed into drugs for preventing and treating tumor diseases, especially liver cancer, lung cancer and neuroblastoma.

8 Claims, 5 Drawing Sheets

SUBSTANCE HAVING TYROSINE KINASE INHIBITORY ACTIVITY AND PREPARATION METHOD AND USE THEREOF

CROSS-REFERENCE TO RELATED APPLICATIONS

The present application is a national phase entry under 35 U.S.C §371 of International Application No. PCT/CN2013/000720 filed Jun. 20, 2013, which is hereby incorporated herein by reference.

TECHNICAL FIELD

The present disclosure pertains to the medical and pharmaceutical field, and relates to a new class of compounds, and particularly, to a class of 2-indolone derivatives (general formula I), geometric isomers and pharmaceutical salts thereof, and methods for preparing these compounds, and their use in the prevention and treatment of tumor diseases.

BACKGROUND ART

Tumor is a major disease jeopardizing human health, and the global number of annual deaths due to malignant tumor is the second largest among all diseases. Research on anti-tumor drugs has been drawing close attention all around the world. Traditional chemotherapy drugs may block cell division non-specifically or cause cell death directly, thus destroying human normal cells while killing tumor cells. With thorough understanding of the mechanism behind formation and development of tumor, the development of novel drugs with high efficacy, low toxicity and high specificity by targeting essential enzymes in the signaling pathway of tumor cell has become an important trend in current researches of anti-tumor drugs.

Among various targets of anti-tumor drugs, protein tyrosine kinase signaling pathway is closely related to the proliferation and differentiation of tumor cells. Interfering or blocking tyrosine kinase signaling pathway has become a focus of current researches and developments of anti-tumor drugs. Each year, a large number of studies are reported. A variety of tyrosine kinase inhibitors have come into the market, such as Gefitinib which is a tyrosine kinase inhibitor for treating lung cancer, Gleevec which is a tyrosine kinase inhibitor for treating chronic myelogenous leukemia, and Sunitinib for treating advanced renal cell carcinoma, etc. They can act on multiple targets including epidermal growth factor receptor (EGFR) and vascular endothelial growth factor receptor (VEGFR), etc. More other tyrosine kinase inhibitors under developments have entered into different stages of clinical studies.

Anti-tumor drug Gefitinib (Iressa) is a tyrosine kinase inhibitor developed by AstraZeneca, UK. It was approved for use in advanced or metastatic non-small cell lung cancer (NSCLC) in the United States in 2003, and it was approved for marketing in China in 2005. Clinical studies were carried out in five Chinese clinical study sites, to assess the objective response rate of Gefitinib tablet 250 mg/day in NSCLC patients who have received chemotherapy previously. A total of 159 subjects received at least one dose of Gefitinib tablet 250 mg. The results showed that the objective response rate was 27.0% (according to Gefitinib's instruction, baike.soso.com/v8292080.htm). This indicated that the drug resulted in a low efficacy. Therefore, keeping on looking for efficient tyrosine kinase inhibitors has important practical significance.

SUMMARY

The object of the present disclosure is to provide substances capable of inhibiting tyrosine kinase activity and drugs having anti-tumor effect.

The first aspect of the present disclosure relates to substances having tyrosine kinase inhibitory activity, i.e, compounds of general formula I, geometric isomers and pharmaceutically acceptable salts thereof:

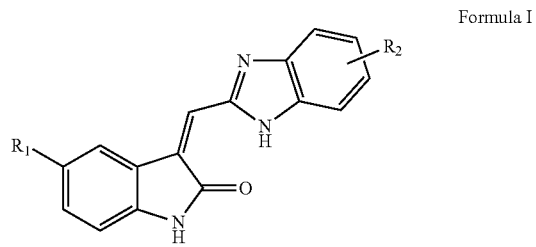

Formula I wherein, $R_2$ is hydrogen or halogen; $R_1$ is hydrogen or $-SO_2NR_3R_4$ in which $R_3$ is hydrogen or methyl, $R_4$ is phenyl, cyclohexyl, halogen-substituted phenyl, methylphenyl, ethylphenyl, ethoxyphenyl, hydroxyphenyl or β-naphthyl.

The compounds of formula I include any one of the following:
3-(1H-benzimidazol-2-methylene)-5-(β-naphthylaminosulfo)-2-indolone (Indo 1);
3-(1H-benzimidazol-2-methylene)-5-(3-chloro-4-fluorophenylaminosulfo)-2-indolone (Indo 2);
3-(1H-benzimidazol-2-methylene)-5-(N-methylphenylaminosulfo)-2-indolone (Indo 3);
3-(1H-benzimidazol-2-methylene)-5-(cyclohexylaminosulfo)-2-indolone (Indo 4);
3-(1H-benzimidazol-2-methylene)-5-(2-methylphenylaminosulfo)-2-indolone (Indo 5);
3-(1H-benzimidazol-2-methylene)-5-(4-chlorophenylaminosulfo)-2-indolone (Indo 6);
3-(1H-benzimidazol-2-methylene)-5-(4-hydroxyethylphenylaminosulfo)-2-indolone (Indo 7);
3-(1H-benzimidazol-2-methylene)-5-(4-methylphenylaminosulfo)-2-indolone (Indo 8);
3-(1H-benzimidazol-2-methylene)-5-(4-ethoxyphenylaminosulfo)-2-indolone (Indo 9).

According to structure-activity relationship of tyrosine kinase inhibitors, a series of compounds are designed and tyrosine kinase inhibitory activity of the synthesized compounds is evaluated to demonstrate that these compounds have good tyrosine kinase inhibitory activity.

The compounds of the present disclosure may effectively inhibit the tyrosine kinase activity, and thus have potential anti-tumor activity and may be used for anti-tumor therapy.

Pharmaceutical compositions comprising geometric isomers, pharmaceutically acceptable salts, hydrates or solvates of the above compounds, and pharmaceutically acceptable carriers or excipients are also within the scope of the present disclosure. Specifically, the pharmaceutical compositions comprise:

isomers or hydrates of the above compounds, such as syn or anti compounds;

pharmaceutically acceptable salts of the above compounds, including sulfate, pyrosulfate, bisulfate, sulfite, bisulfite, phosphate, monohydrogenphosphate, dihydrogenphosphate, metaphosphate, pyrophosphate, hydrochloride, bromide, iodide, acetate, propionate, caprylate, acrylate, formate, isobutyrate, enanthate, decanoate, propiolate, oxalate, malonate, succinate, suberate, sebacate, fumarate, maleate, 2-butyne-1,4-dioate, 3-cyclohexyne-2,5-dioate, benzoate, chlorobenzoate, phenylacetate, phenylpropionate, phenylbutyrate, citrate, lactate, hippurate, 3-hydroxybutyrate, glycolate, maleate, tartrate, methanesulfonate, propanesulfonate, naphthalene-1-sulfonate, naphthalene-2-sulfonate, mandelate, glutamate, argininate, lysinate, etc. In view of medicinal and pharmaceutical purposes of compounds of the present disclosure, the hydrochlorides and phosphates are particularly preferred.

Another aspect of the present disclosure relates to the method for preparing the compounds of general formula I, comprising:

mixing a compound of formula II and a compound of formula III in methanol, ethanol or isopropanol, or a mixed solution thereof,

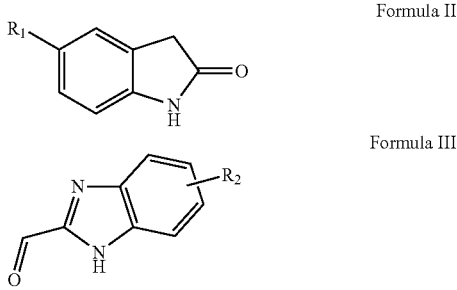

Formula II

Formula III adding thereto a basic or acidic catalyst, and refluxing to obtain the desired product, wherein $R_1$ and $R_2$ are defined as above.

During the preparation, the basic catalyst is selected from inorganic basic compounds, including potassium hydroxide, sodium hydroxide, ammonia, calcium oxide and aqueous solution thereof; organic amines, including triethylamine, piperidine, dimethylaminopyridine, 2,4,5-trimethylpyridine or pyridine, etc. The acidic catalyst is selected from inorganic acids, including hydrochloric acid, and phosphoric acid; organic acids, including p-toluenesulfonic acid and acetic acid, etc.

Pharmaceutical compositions comprising one or more substances having tyrosine kinase inhibitory activity above in a pharmaceutically effective amount and pharmaceutically acceptable carriers or excipients are also within the scope of the present disclosure. The pharmaceutical compositions containing an effective amount of the compound of the present disclosure may be prepared with pharmaceutical carriers well known to those skilled in the art.

A further aspect of the present disclosure relates to use of the compounds of general formula I, geometric isomers or pharmaceutically acceptable salts thereof, or the compositions in the manufacture of tyrosine kinase inhibitor drugs or anti-tumor drugs.

The present disclosure also involves use of prodrugs prepared from said compounds for treating, preventing, inhibiting or relieving tumor and associated diseases in mammals, preferably human. The use comprises administering a pharmaceutically effective amount of the drugs of the present disclosure or pharmaceutical compositions thereof to a mammal in need of the treatment.

The use is intended to induce tumor cell apoptosis, inhibit tumor angiogenesis, and prevent chemotherapy resistance of tumors and malignant metastasis of tumors.

The tumor is breast cancer, lung cancer, skin cancer, colon cancer, prostate cancer, pancreatic cancer, liver cancer, gastric cancer, head and neck cancer, glioma, neuroblastoma, melanoma, renal carcinoma or leukemia.

The tyrosine kinase inhibitor drugs are drugs for treating disorders associated with c-Met or Trk signaling pathway.

Disorders associated with c-Met signaling pathway include, but are not limited to liver cancer, breast cancer, lung cancer, prostate cancer, pancreatic cancer, colon cancer, gastric cancer, head and neck cancer or leukemia, etc.

Disorders associated with Trk signaling pathway include, but are not limited to breast cancer, lung cancer, skin cancer, gastric cancer, glioma, neuroblastoma, melanoma, renal carcinoma or leukemia.

A further aspect of the present disclosure relates to use of 3-(1H-benzimidazol-2-methylene)-5-(2-methylphenylaminosulfo)-2-indolone (Indo 5) in the manufacture of the tyrosine kinase inhibitors or anti-tumor drugs. The tumor includes, but not limited to breast cancer, lung cancer, colon cancer, prostate cancer, pancreatic cancer, liver cancer, gastric cancer, head and neck cancer, glioma, melanoma, renal carcinoma and leukemia, etc., particularly disorders associated with Trk or c-Met signaling pathway, including, but not limited to liver cancer, breast cancer, lung cancer, prostate cancer, pancreatic cancer, colon cancer, gastric cancer, head and neck cancer or leukemia, particularly liver cancer, lung cancer or neuroblastoma.

Substances of the present disclosure having tyrosine kinase inhibitory activity may be provided via injection, oral or parenteral administration. The substances may be in the form of tablet, pill, powder mixture, capsule, coated agent, solution, emulsion, dispersion, injection or suppository, or any other suitable form. These formulations are prepared through methods well known by those skilled in the art. Adjuvants used for preparation of tablet, capsule, and coated agent are conventional adjuvants, such as starch, gelatin, arabic gum, silica, polyethylene glycol, and a solvent used in liquid dosage forms, such as water, ethanol, propylene glycol, and vegetable oils such as corn oil, peanut oil, and olive oil, etc. Formulations containing the compounds of the present disclosure may additionally comprise other adjuvants, such as surfactant, lubricant, disintegrant, preservative, flavoring agent, or pigment, etc.

When using a drug related to the compounds of the present disclosure, in order to achieve the desired biological effect, the pharmaceutically effective amount desired depends on various factors, such as the specific compound selected, the intended use, the route of administration and the clinical condition of the patient. The pharmaceutically effective amount may be determined with reference to the existing tyrosine kinase inhibitor—Gefitinib (Iressa) which is an anti-tumor agent, for example, 250 mg/day.

The present disclosure provides a class of 2-indolone derivatives having tyrosine kinase inhibitory activity, geometric isomers and pharmaceutically acceptable salts thereof, and preparation method and use of these compounds. Through evaluation of tyrosine kinase inhibitory activity, it has been demonstrated that these compounds have excellent tyrosine kinase inhibitory activity, and thus have potential anti-tumor activity. Drugs for the prevention and treatment of tumor diseases (anti-tumor drugs) may be prepared by using the compounds as the active ingredients. The present disclosure will play an important role in anti-tumor therapy and have a promising application.

The present disclosure will be described in detail in combination with the specific examples.

DETAILED DESCRIPTION

Figure 1:
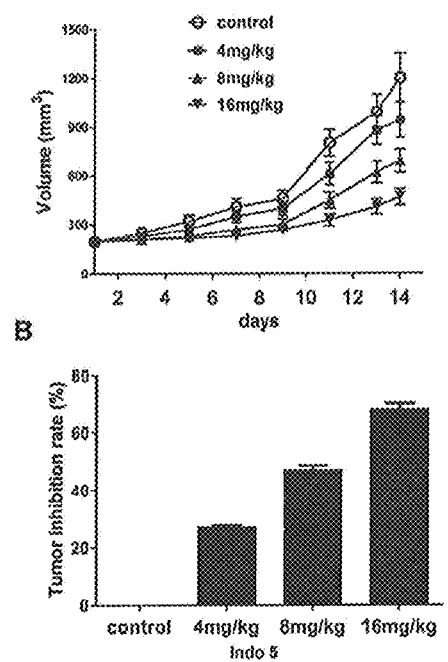
FIG. 1 shows the inhibition of different doses of the compound Indo 5 on the tumor in HepG2 tumor-bearing mice.

Unless otherwise particularly specified, the percentage concentration is weight/volume (W/V) percentage concentration or volume/volume (V/V) percentage concentration.

The approach for obtaining various biological materials as described in the examples is only intended to provide an experimentally obtaining approach for the purpose of specific disclosure, and should not be construed as a limitation to the source of the biological materials of the present disclosure. In fact, there are many sources from which the biological material used may be obtained. Any biological material, which may be obtained without violating any law or ethic, may be used as an alternative in accordance with hint in the examples.

The examples are implemented on the basis of the technical solution of the present disclosure and provide detailed methods for implementation and specific procedures. The examples will be helpful to understand the present disclosure, but the protection scope of the present disclosure is not limited to the following examples.

Example 1

3-(1H-benzimidazol-2-methylene)-5-(β-naphthylaminosulfo)-2-indolone (Indo 1)

0.17 g (0.5 mmol) 5-(B-naphthylaminosulfo)-2-indolone and 0.10 g (0.685 mmol) 1H-benzimidazol-2-formaldehyde were suspended in 6 mL anhydrous ethanol, followed by addition of 2 drops of piperidine. The mixture was heated and refluxed in an oil bath for 30 min. A large quantity of yellow solid was precipitated, filtered, and washed with anhydrous ethanol, to obtain 0.18 g pale yellow solid, with a yield of 77.3%.

Analytical result by nuclear magnetic resonance (NMR) spectroscopy: $^1$H-NMR (DMSO-$d_6$) δ(ppm): δ13.81 (s, 1H), 11.68 (s, 1H), 10.51 (s, 1H), 8.48 (s, 1H), 8.13 (s, 1H), 7.58-7.82 (m, 6H), 7.64 (s, 1H, J=8.4 Hz), 7.29-7.46 (m, 5H), 7.05 (d, 1H, J=8.4 Hz). ESI-MS m/z: 465 [M-H]$^+$ (100). Analysis showed that, the pale yellow solid is 3-(1H-benzimidazol-2-methylene)-5-(β-naphthylaminosulfo)-2-indolone, the structural formula of which is shown in Formula I, wherein $R_1$ is β-naphthylaminosulfo, and $R_2$ is hydrogen.

Example 2

3-(1H-benzimidazol-2-methylene)-5-(3-chloro-4-fluorophenylaminosulfo)-2-indolone (Indo 2)

0.17 g (0.5 mmol) 5-(3-chloro-4-fluorophenylaminosulfo)-2-indolone and 0.10 g (0.685 mmol) 1H-benzimidazol-2-formaldehyde were suspended in 6 mL anhydrous ethanol, followed by addition of 2 drops of piperidine. The mixture was heated and refluxed in an oil bath for 30 min. A large quantity of yellow solid was precipitated, filtered, and washed with anhydrous ethanol, to obtain 0.15 g pale yellow solid, with a yield of 64.1%.

Analytical result by NMR spectroscopy: $^1$H-NMR (DMSO-$d_6$) δ (ppm): δ13.82 (s, 1H), 11.74 (s, 1H), 10.45 (s, 1H), 8.38 (s, 1H), 8.14 (s, 1H), 7.78-7.84 (q, 2H), 7.69 (d, 1H), 7.26-7.38 (m, 4H), 7.17-7.15 (m, 1H), 7.09 (d, 1H, J=8.4 Hz). ESI-MS m/z: 467 [M-H]$^+$ (100). Analysis showed that, the pale yellow solid is 3-(1H-benzimidazol-2-methylene)-5-(3-chloro-4-fluorophenylaminosulfo)-2-indolone, the structural formula of which is shown in Formula I, wherein $R_1$ is 3-chloro-4-fluorophenylaminosulfo, and $R_2$ is hydrogen.

Example 3

3-(1H-benzimidazol-2-methylene)-5-(N-methylphenylaminosulfo)-2-indolone (Indo 3)

0.15 g (0.5 mmol) 5-(N-methylphenylaminosulfo)-2-indolone and 0.10 g (0.685 mmol) 1H-benzimidazol-2-formaldehyde were suspended in 6 mL anhydrous ethanol, followed by addition of 2 drops of piperidine. The mixture was heated and refluxed in an oil bath for 30 min. A large quantity of yellow solid was precipitated, filtered, and washed with anhydrous ethanol, to obtain 0.14 g pale yellow solid, with a yield of 65.1%.

Analytical result by NMR spectroscopy: $^1$H-NMR (DMSO-$d_6$) δ (ppm): δ13.83 (s, 1H), 11.73 (s, 1H), 8.24 (s, 1H), 8.20 (s, 1H), 7.81 (b, 2H), 7.27-7.37 (m, 6H), 7.17 (s, 1H), 7.15 (s, 1H), 7.05 (d, 1H, J=8.4 Hz), 3.21 (s, 3H). ESI-MS m/z: 429 [M-H]$^+$ (100). Analysis showed that, the pale yellow solid is 3-(1H-benzimidazol-2-methylene)-5-(N-methylphenylaminosulfo)-2-indolone, the structural formula of which is shown in Formula I, wherein $R_1$ is N-methylphenylaminosulfo, and $R_2$ is hydrogen.

Example 4

3-(1H-benzimidazol-2-methylene)-5-(cyclohexylaminosulfo)-2-indolone (Indo 4)

0.15 g (0.5 mmol) 5-(cyclohexylaminosulfo)-2-indolone and 0.10 g (0.685 mmol) 1H-benzimidazol-2-formaldehyde were suspended in 6 mL anhydrous ethanol, followed by addition of 2 drops of piperidine. The mixture was heated and refluxed in an oil bath for 30 min. A large quantity of yellow solid was precipitated, filtered, and washed with anhydrous ethanol, to obtain 0.17 g pale yellow solid, with a yield of 80.6%.

Analytical result by NMR spectroscopy: $^1$H-NMR (DMSO-$d_6$) δ (ppm): δ13.86 (s, 1H), 11.68 (s, 1H), 8.35 (s, 1H), 8.08 (s, 1H), 7.76-7.84 (m, 3H), 7.48 (d, 1H, J=7.2 Hz), 7.66 (d, 1H, J=6.4 Hz), 7.38 (t, 1H), 7.31 (t, 1H), 7.10 (d, 1H, J=8.0 Hz), 3.02 (b, 1H), 1.60 (b, 5H), 1.50 (b, 5H). ESI-MS m/z: 421 [M-H]$^+$ (100). Analysis showed that, the pale yellow solid is 3-(1H-benzimidazol-2-methylene)-5-(cyclohexylaminosulfo)-2-indolone, the structural formula of which is shown in Formula I, wherein $R_1$ is cyclohexylaminosulfo, and $R_2$ is hydrogen.

Example 5

3-(1H-benzimidazol-2-methylene)-5-(2-methylphenylaminosulfo)-2-indolone (Indo 5)

0.15 g (0.5 mmol) 5-(2-methylphenylaminosulfo)-2-indolone and 0.10 g (0.685 mmol) 1H-benzimidazol-2-formaldehyde were suspended in 6 mL anhydrous ethanol, followed by addition of 2 drops of piperidine. The mixture was heated and refluxed in an oil bath for 30 min. A large quantity of yellow solid was precipitated, filtered, and washed with anhydrous ethanol, to obtain 0.12 g pale yellow solid, with a yield of 55.8%.

Analytical result by NMR spectroscopy: $^1$H-NMR (DMSO-$d_6$) δ (ppm): δ13.82 (s, 1H), 11.70 (s, 1H), 9.44 (s, 1H), 8.20 (s, 1H), 8.00 (s, 1H), 7.82 (d, 1H, J=8.0 Hz), 7.78 (d, 1H, J=8.0 Hz), 7.61 (dd, 1H, J=16.8 Hz), 7.38 (t, 1H), 7.30 (t, 1H), 7.00-7.15 (m, 5H), 2.09 (s, 3H). ESI-MS m/z: 429 [M-H]$^+$ (100). Analysis showed that, the pale yellow solid is 3-(1H-benzimidazol-2-methylene)-5-(2-methylphenylaminosulfo)-2-indolone, the structural formula of which is shown in Formula I, wherein $R_1$ is 2-methylphenylaminosulfo, and $R_2$ is hydrogen.

Example 6

3-(1H-benzimidazol-2-methylene)-5-(4-chlorophenylaminosulfo)-2-indolone (Indo 6)

0.16 g (0.5 mmol) 5-(4-chlorophenylaminosulfo)-2-indolone and 0.10 g (0.685 mmol) 1H-benzimidazol-2-formaldehyde were suspended in 6 mL anhydrous ethanol, followed by addition of 2 drops of piperidine. The mixture was heated and refluxed in an oil bath for 30 min. A large quantity of yellow solid was precipitated, filtered, and washed with anhydrous ethanol, to obtain 0.18 g pale yellow solid, with a yield of 80.0%.

Analytical result by NMR spectroscopy: $^1$H-NMR (DMSO-$d_6$) δ(ppm): δ13.81 (s, 1H), 11.70 (s, 1H), 10.36 (s, 1H), 8.36 (s, 1H), 8.10 (s, 1H), 7.80 (b, 2H), 7.70 (dd, 1H, J=16.4 Hz), 7.38 (b, 2H), 7.30 (d, 2H, J=13.6 Hz), 7.17 (d, 2H, J=11.6 Hz), 7.08 (d, 1H, J=8.4 Hz). ESI-MS m/z: 449[M-H]$^+$ (100). Analysis showed that, the pale yellow solid is 3-(1H-benzimidazol-2-methylene)-5-(4-chlorophenylaminosulfo)-2-indolone, the structural formula of which is shown in Formula I, wherein $R_1$ is 4-chlorophenylaminosulfo, $R_2$ is hydrogen.

Example 7

3-(1H-benzimidazol-2-methylene)-5-(4-hydroxyethylphenylaminosulfo)-2-indolone (Indo 7)

0.16 g (0.5 mmol) 5-(4-hydroxyethylphenylaminosulfo)-2-indolone and 0.10 g (0.69 mmol) 1H-benzimidazol-2-formaldehyde were suspended in 6 mL anhydrous ethanol, followed by addition of 2 drops of piperidine. The mixture was heated and refluxed in an oil bath for 30 min. A large quantity of yellow solid was precipitated, filtered, and washed with anhydrous ethanol, to obtain 0.16 g pale yellow solid, with a yield of 69.6%.

Analytical result by NMR spectroscopy: $^1$H-NMR (DMSO-$d_6$) δ(ppm): δ13.83 (s, 1H), 11.71 (s, 1H), 10.12 (s, 1H), 8.33 (s, 1H), 8.06 (s, 1H), 7.81 (b, 2H), 7.70 (dd, 1H, J=16.4 Hz), 7.34 (d, 2H), 7.06-7.08 (m, 5H), 4.60 (s, 1H), 4.49 (d, 2H), 2.59 (t, 3H). ESI-MS m/z: 459[M-H]$^+$ (100). Analysis showed that, the pale yellow solid is 3-(1H-benzimidazol-2-methylene)-5-(4-hydroxyethylphenylaminosulfo)-2-indolone, the structural formula of which is shown in Formula I, wherein $R_1$ is 4-hydroxyethylphenylaminosulfo, $R_2$ is hydrogen.

Example 8

3-(1H-benzimidazol-2-methylene)-5-(4-methylphenylaminosulfo)-2-indolone (Indo 8)

0.15 g (0.5 mmol) 5-(4-methylphenylaminosulfo)-2-indolone and 0.10 g (0.685 mmol) 1H-benzimidazoyl-2-formaldehyde were suspended in 6 mL anhydrous ethanol, followed by addition of 2 drops of piperidine. The mixture was heated and refluxed in an oil bath for 30 min. A large quantity of yellow solid was precipitated, filtered, and washed with anhydrous ethanol, to obtain 0.18 g pale yellow solid, with a yield of 83.7%.

Analytical result by NMR spectroscopy: $^1$H-NMR (DMSO-$d_6$) δ(ppm): δ13.82 (s, 1H), 11.70 (s, 1H), 10.06 (s, 1H), 8.32 (s, 1H), 8.06 (s, 1H), 7.83 (d, 1H, J=8.0 Hz), 7.79 (d, 1H, J=8.4 Hz), 7.67 (dd, 1H, J=16.8 Hz), 7.38 (t, 1H), 7.31 (t, 1H), 7.30 (d, 2H, J=13.6 Hz), 7.06 (d, 2H, J=8.4 Hz), 7.03 (s, 4H), 2.17 (s, 3H). ESI-MS m/z: 429[M-H]$^+$ (100). Analysis showed that, the pale yellow solid is 3-(1H-benzimidazol-2-methylene)-5-(4-methylphenylaminosulfo)-2-indolone, the structural formula of which is shown in Formula I, wherein $R_1$ is 4-methylphenylaminosulfo, $R_2$ is hydrogen.

Example 9

3-(1H-benzimidazol-2-methylene)-5-(4-ethoxyphenylaminosulfo)-2-indolone (Indo 9)

0.16 g (0.5 mmol) 5-(4-ethoxyphenylaminosulfo)-2-indolone and 0.10 g (0.685 mmol) 1H-benzimidazoyl-2-formaldehyde were suspended in 6 mL anhydrous ethanol, followed by addition of 2 drops of piperidine. The mixture was heated and refluxed in an oil bath for 30 min. A large quantity of yellow solid was precipitated, filtered, and washed with anhydrous ethanol, to obtain 0.13 g pale yellow solid, with a yield of 58.3%.

Analytical result by NRM spectroscopy: $^1$H-NMR (DMSO-$d_6$) δ(ppm): δ13.82 (s, 1H), 11.71 (s, 1H), 9.83 (s, 1H), 8.24 (s, 1H), 8.02 (s, 1H), 7.83 (d, 1H, J=8.0 Hz), 7.79 (d, 1H, J=8.0 Hz), 7.62 (dd, 1H, J=16.4 Hz), 7.38 (t, 1H), 7.31 (t, 1H), 7.05 (d, 1H, J=8.4 Hz), 7.01 (d, 2H, J=9.2 Hz), 7.05 (d, 2H, J=8.8 Hz), 3.90 (q, 2H), 1.24 (t, 3H). ESI-MS m/z): 459 [M-H]$^+$ (100). Analysis showed that, the pale yellow solid is 3-(1H-benzimidazol-2-methylene)-5-(4-ethoxyphenylaminosulfo)-2-indolone, the structural formula of which is shown in Formula I, wherein $R_1$ is 4-ethoxyphenylaminosulfo, and $R_2$ is hydrogen.

Experimental Example 1

Tyrosine Kinase Inhibitory Activity of 2-Indolone Derivatives

Material:
Tyrosine kinase buffer: 10 mL 1M HEPES (pH 7.5), 0.4 mL 5% BSA/PBS, 0.2 mL 0.1M $Na_3VO_4$, and 1 mL 5M NaCl were added to 88.4 mL double distilled water (DDW) (HEPES: Amresco; $Na_3VO_4$: Sigma).

ATP: Adenosine triphosphate, Amresco.

Extraction of tissue extract PTK: mouse brain tissue was quickly removed and weighed, followed by addition of five-fold volumes of pre-cooled homogenization buffer for homogenization. After centrifugation at 4° C., 1,000 g for 10 min, nuclei and cell debris were removed. The supernatant S1 was collected and centrifuged at 4° C., 10,000 g for 20 min, and then the supernatant S2 was collected. The precipitate P2, which represents the crude membrane protein fraction, was retained. S2 included cytoplasmic protein, and was used for testing protein tyrosine kinase (PTK) activity. In the detection of the membrane protein fraction, two-fold volumes of lysis buffer was added to P2, and the resultant was placed on ice for 10 min and centrifuged at 4° C., 10,000 g for 10 min. The supernatant S3, which represents the crude membrane protein including soluble membrane protein, was collected for testing PTK activity. Protein content in cytoplasm or membrane protein was detected by using BCA protein concentration kit (purchased from Beyotime Institute of Biotechnology). The tissue extract was stored at −70° C.

Coating of 96-well plate: PTK substrate was dissolved and added in an amount of 100 μl to each well. The plate was covered with its lid, and incubated at 4° C. overnight (10-12 hours). Then it was washed with 200 μl elution buffer once, and dried at 37° C. for 2 h. After that, it was washed with 10 mM PBS once, dried at room temperature, and then stored at 4° C. for further use.

Groups: blank control: 80 μl 1× tyrosine kinase buffer containing ATP+20 μl 1× tyrosine kinase buffer; negative control: 80 μl 1× tyrosine kinase buffer containing ATP+10 μl 1× tyrosine kinase buffer+7 μl tissue extract+3 μl 1× tyrosine kinase buffer; positive control: 80 μl 1× tyrosine kinase buffer containing ATP+10 μl Gefitinib+7 μl tissue extract+3 μl 1× tyrosine kinase buffer (first, the positive drug was allowed to interact with the tyrosine kinase tissue extract at room temperature for 10 min, and meanwhile the tissue extract for the negative control group was also placed at room temperature for 10 min, and then 80 μl 1× tyrosine kinase buffer containing ATP was added to respective groups); vehicle control: 80 μl 1× tyrosine kinase buffer containing ATP+10 μl DMSO+7 μl tissue extract+3 μl 1× tyrosine kinase buffer; drugs to be screened: 80 μl 1× tyrosine kinase buffer containing ATP+10 μl drug to be tested +7 μl tissue extract+3 μl 1× tyrosine kinase buffer.

PTK activity assay: 1× tyrosine kinase buffer was prepared by evenly mixing 1 mL (10×) tyrosine kinase buffer with 9 mL DDW. The tissue extract was diluted with 1× tyrosine kinase buffer appropriately, mixed with it gently and evenly, and placed on ice. ATP stock solution was dissolved by evenly mixing 48 μl ATP stock solution with 1 mL 1× tyrosine kinase buffer, and placed on ice. The microplate reader was added in respective wells with the groups formulated as above, covered with the lid, and incubated at room temperature for 30 min. The microplate reader was washed with 200 μl elution buffer and tapped until the residual buffer was removed, and this procedure was repeated for five times. To each well, 100 μl antibody diluent (antibody elution buffer diluted at a ratio of 1:2000) was added. The reader was covered with the lid, and incubated at room temperature for 30 min. OPD solution was prepared by addition of 4 mg OPD into a mixture of 4.86 mL 0.1 mol/L citric acid solution and 5.14 mL 0.2 mol/L $Na_2HPO_4$ solution, followed by addition of 50 μl 30% $H_2O_2$ to allow for complete dissolution, and then was protected from light. The antibody solution was removed. The reader was washed with 200 μl elution buffer and tapped until the residual buffer was removed, and this procedure was repeated for five times. 100 μl freshly prepared OPD was added, and reacted at room temperature light tight for precisely 7 min. Positive wells showed an orange color. 100 μl 2.5 N $H_2SO_4$ was added to terminate the reaction. OD was measured at 492 nm.

Sample screening: Samples were screened preliminarily. The effect of the samples on protein tyrosine kinase activity was tested, and the inhibition rate was calculated. Inhibition rate (%)=$(OD_{negative\ control}-OD_{sample})/(OD_{negative\ control}^*-OD_{blank})\times 100\%$; * while calculating inhibition rate of positive drugs, $OD_{negative\ control}$ in the equation was replaced with $OD_{vehicle\ control}$, to exclude the influence of DMSO on PTK activity.

Results: See Table 1. Table 1 illustrates results from the drug group (the Compound Nos. were obtained from the corresponding examples) and positive drug group (Gefitinib).

TABLE 1

Inhibition rate of compounds of the present disclosure on tyrosine kinase

| Compound No. | Inhibition rate | Compound No. | Inhibition rate |
|---|---|---|---|
| Gefitinib | 40.2% | Indo 1 | 51.2% |
| Indo 2 | 45.2% | Indo 3 | 55.9% |
| Indo 4 | 60.7% | Indo 5 | 53.4% |
| Indo 6 | 55.0% | Indo 7 | 58.2% |
| Indo 8 | 49.9% | Indo 9 | 51.3% |

Data of Table 1 showed that: the positive drug Gefitinib significantly inhibited tyrosine kinase activity at 400 μM, with an inhibition rate of 40.2%, while all compounds of the examples of the present disclosure showed strong inhibition on tyrosine kinase activity at the same concentration, with an inhibition rate above 45%, which are comparable with or superior over the positive control drug, indicating that these compounds may potentially prevent and treat tumors with high expression of tyrosine kinase.

Experimental Example 2

In Vitro Antitumor Activity of 2-Indolone Derivatives of the Present Disclosure

Method: 14 cell lines (MKN-45 cells, MHCC97-L cells, MHCC97-H cells, HLE cells, HepG2 cells, 7721 cells, L02 cells, A375 cells, H460 cells, A549 cells, SK-N-SH cells, MCF-7 cells, K562 cells, and Ba/F3-Tpr-Met cells (pre-B cells which are malignantly transformed by the c-Met constitutive active mutant Tpr-Met) were seeded into 96-well plate at 1×10⁴ cells/well, and each well was added with 150 μl DMEM medium (purchased from Invitrogen) containing 10% fetal bovine serum (purchased from Hyclone). When cell adherent was observed, different concentrations of 2-indolone derivatives (concentrations at 0.1-10 μM) were added, in addition to the negative control (vehicle control group) and blank control (medium group). After culture at 37° C., 5% $CO_2$ for 72 hours, MTS reagent (Promega Corporation) were added for further culture for 2-4 h. OD values were detected with microplate reader at a wavelength of 450 nm, and IC50 (a concentration of the compound at which the inhibition rate of cell proliferation reaches 50%) was calculated with software SPSS.

The results were shown in Table 2 (IC50 (μM) indicates a concentration of the compound at which the inhibition rate of cell proliferation reaches 50%). Except that the compounds barely affected the proliferation of normal liver cell L02, they showed significant inhibition on the other tumor cell lines, suggesting that 2-indolone derivatives of the present disclosure have significant in vitro anti-tumor activity and have no adverse effect on normal cells.

TABLE 2

In vitro antitumor activity of 2-indolone derivatives of the present disclosure

| Cell line | Tissue origin | IC50 (μM) | | | | |
|---|---|---|---|---|---|---|
| | | Indo 1 | Indo 2 | Indo 3 | Indo 4 | Indo 5 |
| MKN-45 | Gastric cancer | 1.97 | 2.13 | 1.29 | 0.94 | 1.549 |
| MHCC97-L | hepatocellular cancer | 1.54 | 1.87 | 1.11 | 0.64 | 1.206 |
| MHCC97-H | hepatocellular cancer | 1.38 | 1.67 | 0.82 | 0.54 | 1.029 |
| H460 | Lung cancer | 1.54 | 1.78 | 1.05 | 0.78 | 1.067 |
| HLE | hepatocellular cancer | 6.31 | 6.792 | 4.72 | 3.58 | 5.228 |
| HepG2 | hepatocellular cancer | 6.47 | 6.982 | 4.79 | 3.69 | 5.665 |
| A375 | Skin cancer | 3.18 | 2.476 | 1.47 | 0.97 | 1.873 |
| MCF-7 | Breast cancer | 1.72 | 1.953 | 0.96 | 1.46 | 1.281 |
| A549 | Lung cancer | 2.89 | 3.156 | 1.54 | 2.32 | 2.193 |
| SK-N-SH | Neuroblastoma | 1.35 | 1.793 | 0.85 | 0.54 | 1.187 |
| K562 | Leukemia | 3.02 | 3.267 | 2.07 | 1.34 | 2.583 |
| L02 | hepatic cells | 24.77 | 23.69 | 22.19 | 26.77 | 20.88 |
| Ba/F3-Tpr-Met | Pre-B cell | 5.31 | 5.93 | 3.87 | 2.54 | 4.791 |

| Cell line | Tissue origin | IC50 (μM) | | | |
|---|---|---|---|---|---|
| | | Indo 6 | Indo 7 | Indo 8 | Indo 9 |
| MKN-45 | Gastric cancer | 1.38 | 1.13 | 2.02 | 1.72 |
| MHCC97-L | hepatocellular cancer | 1.06 | 0.97 | 1.68 | 1.31 |
| MHCC97-H | hepatocellular cancer | 0.91 | 0.69 | 1.53 | 1.17 |
| H460 | Lung cancer | 0.94 | 0.92 | 1.63 | 1.25 |
| HLE | hepatocellular cancer | 4.87 | 4.36 | 6.58 | 5.91 |
| HepG2 | hepatocellular cancer | 5.18 | 4.25 | 6.74 | 5.98 |
| A375 | Skin cancer | 1.65 | 1.22 | 2.35 | 2.12 |
| MCF-7 | Breast cancer | 1.12 | 0.83 | 1.81 | 1.35 |
| A549 | Lung cancer | 1.99 | 1.28 | 3.02 | 2.52 |
| SK-N-SH | Neuroblastoma | 1.06 | 0.67 | 1.57 | 1.22 |
| K562 | Leukemia | 2.21 | 1.67 | 3.11 | 2.64 |
| L02 | hepatic cells | 22.65 | 25.69 | 25.33 | 23.22 |
| Ba/F3-Tpr-Met | Pre-B cell | 4.21 | 3.11 | 5.68 | 4.91 |

Experimental Example 3

In Vivo Antitumor Activity of 2-Indolone Derivative (Indo 5) in Nude Mice Models Inoculated Subcutaneously Method: To evaluate overall in vivo anti-tumor activity of 2-indolone derivatives of the present disclosure, a variety of tumor-bearing nude mice models were established, including HepG2 cells, MHCC97-L, MHCC97-H cells and NCI-H460 cells, and effect of 2-indolone derivatives injected intraperitoneally (Indo 5 as an example) on the growth of tumor in tumor-bearing nude mice was observed.

Establishment of tumor-bearing models: Tumor cells were cultured in T75 flasks until achieving a logarithmical growth. The cells were trypsinized and DMEM medium containing 10% fetal bovine serum was added to terminate trypsinization. The cells were washed with PBS twice, and suspended. Cell concentration was adjusted to 5×10⁷ cells/ml, and 150 μl cell suspension was injected into the right flank of the mice. After inoculation, the tumors in the nude mice were observed every day, and the mice were grouped when the tumors reached a volume of 100 mm³. Each nude mouse was numbered, and the tumor size was measured. The data was entered into EXCEL for sorting and thus excluding extreme values. Random numbers were generated corresponding to the number of the mice, and the mice were randomly grouped using these random numbers.

Administration: intraperitoneal injection was used at doses of 4 mg/kg, 8 mg/kg, and 16 mg/kg, respectively. The vehicle control group was injected with the same volume of DMSO. The mice received treatment once every 24 h, and a total of 6 times of administrations were given. During administration, changes of tumor size (length×width×width/2) were monitored and recorded in a real-time manner, and the results were expressed as mean±standard deviation. Two weeks later, mice were sacrificed, the tumors were isolated and weighed, and the inhibition rate of the compounds on tumor was calculated.

Results: FIG. 1 shows the inhibition of different doses of the compound Indo 5 on the tumor in HepG2 tumor-bearing mice; A represents the tumor volume change curve, and B represents the inhibition rate.

Figure 2:
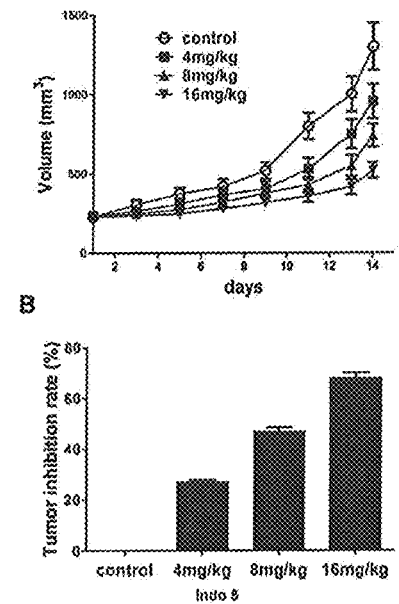
FIG. 2 shows the inhibition of different doses of the compound Indo 5 on the tumor in MHCC97-L tumor-bearing mice.

FIG. 2 shows the inhibition of different doses of the compound Indo 5 on the tumor in MHCC97-L tumor-bearing mice; A represents the tumor volume change curve, and B represents the inhibition rate.

Figure 3:
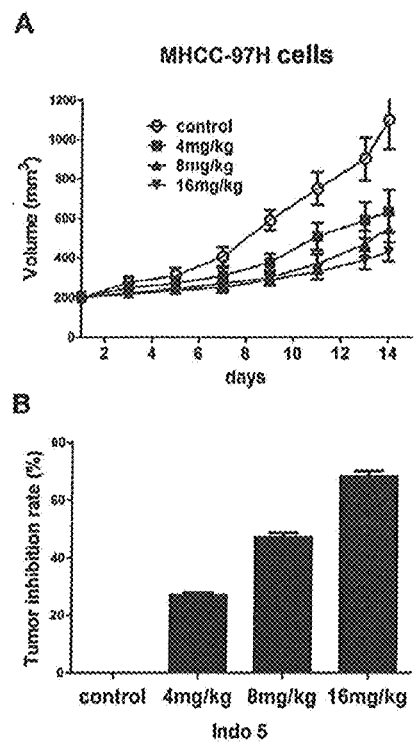
FIG. 3 shows the inhibition of different doses of the compound Indo 5 on the tumor in MHCC97-H tumor-bearing mice.

FIG. 3 shows the inhibition of different doses of the compound Indo 5 on the tumor in MHCC97-H tumor-bearing mice; A represents the tumor volume change curve, and B represents the inhibition rate.

Figure 4:
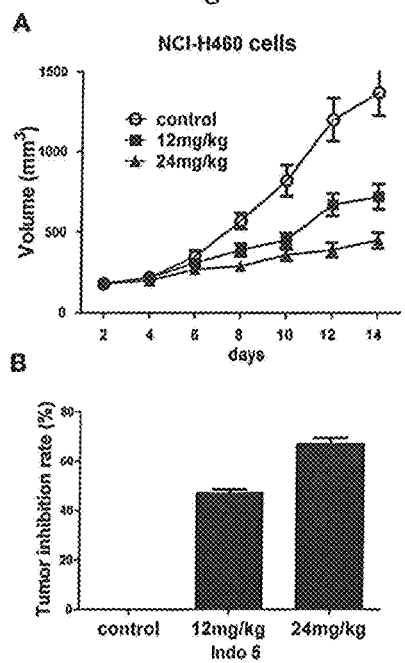
FIG. 4 shows the inhibition of different doses of the compound Indo 5 on the tumor in NCI-H460 tumor-bearing mice.

FIG. 4 shows the inhibition of different doses of the compound Indo 5 on the tumor in NCI-H460 tumor-bearing mice; A represents the tumor volume change curve, and B represents the inhibition rate.

The tumor inhibition rate was calculated by using measurements according to the following equation:

Tumor inhibition rate=(mean weight of control group−mean weight of treatment group)/mean weight of control group×100%

The calculation results showed that the compound Indo 5 via intraperitoneal administration may inhibit tumor cell growth in a dose-dependent manner, and inhibition rates of the compound Indo 5 at the highest dose (16 mg/kg) on in vivo proliferation of HepG2 cells, MHCC97-L/H cells, and NCI-H460 cells were 61%, 68%, 61% and 59%, respectively, indicating that the compound Indo 5 has significant anti-tumor effect on nude mouse models subcutaneously inoculated with a variety of tumor cells.

Experimental Example 4

In Vivo Antitumor Activity of 2-Indolone Derivative (Indo 5) in Liver Orthotopic Tumor Model Establishment of animal models: MHCC-97H cells were cultured in 1640 medium containing 10% fetal bovine serum (supplemented with 100 μl/mL of penicillin and 100 μl/mL of streptomycin) in an incubator at 37° C. and containing 5% $CO_2$. The medium was changed once every 1-2 days. Cells were digested with 0.25% trypsin, and centrifuged at 1,000 r/min for 5 minutes. The supernatant was discarded, and fresh medium was added for subculture. The subcultured tumor cells were digested under a sterile condition and resuspended with sodium chloride injection, and subcutaneously inoculated at the right flank of nude mice. When the subcutaneous tumors in the nude mice grew to a volume about 1,500-2,000 $mm^3$, the tumor mass was removed under a sterile condition, and cut into pieces in a size about 1.0×1.0 mm for future use. Then the nude mice to be inoculated were anesthetized and fixed on the operating table. The abdominal skin was disinfected, and an incision about 1 cm was made in the left upper abdomen to expose the liver, with the surgical site covered. The prepared tumor piece was placed into a dedicated inoculation trocar, and was implanted into the liver by using the trocar. The bleeding site of the wound was treated with sterilized gauze or sterilized cotton swab to stop the bleeding. Then liver which underwent surgery was placed back into the abdominal cavity of mice. The abdominal muscles and skin were sutured with 4/0 gauge surgical needle sequentially. After normal feeding of the mice for 2 weeks, size of liver tumor was observed under B-ultrasound. A tumor of about 100 $mm^3$ indicated that the orthotopic inoculation model was established successfully.

Method: Animal models were randomized into vehicle control group, intraperitoneal low dose group (18 mg/kg), intraperitoneal high dose group (36 mg/kg), and gavage group (36 mg/kg), with 9 mice each group. The mice received treatment once every 24 hours. Intraperitoneal administration was done by intraperitoneal injection. The vehicle control group received DMSO injected intraperitoneally. Six times of administration were given. After the last administration, animals were kept for another 3 weeks, then sacrificed by cervical dislocation, and dissected to obtain liver. Visible tumor was dissected and weighed.

Figure 5:
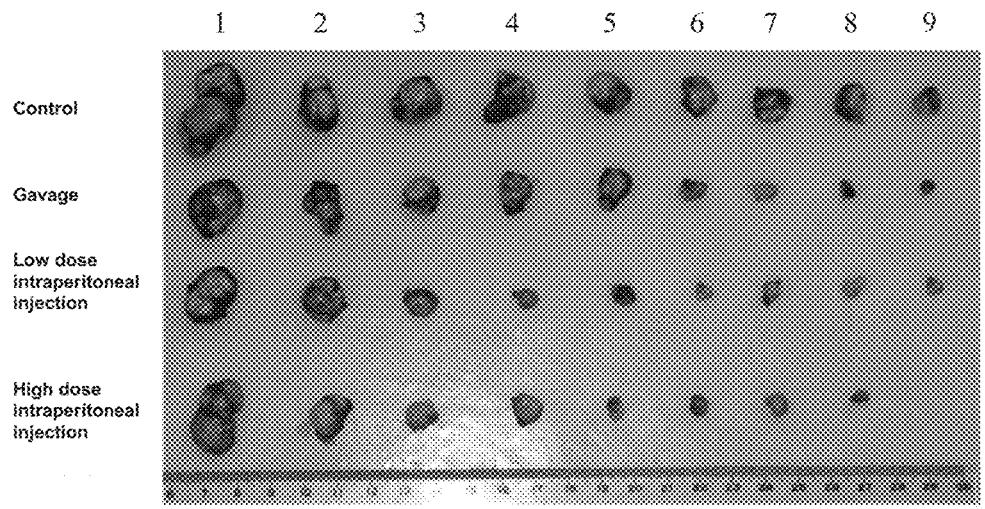
FIG. 5 shows in vivo anti-tumor activity of 2-indolone derivatives (Indo 5) of the present disclosure in a liver orthotopic tumor model.

The results were shown in FIG. 5 and Table 3. FIG. 5 showed photos of tumors dissected from the sacrificed animals of respective groups which each include nine animals (sorted by tumor size, and numbered from 1-9). Liver cancer was gone in one animal (No. 9) of the intraperitoneal high dose group at the end of this experiment. The data suggested that 2-indolone derivative (Indo 5) of the present disclosure could significantly inhibit the ability of hepatoma cell line to orthotopically form liver tumor and showed a dose-dependency. Moreover, the gavage group and the intraperitoneal injection group showed comparable antitumor effect, indicating that the compounds of the present disclosure have anti-tumor effect when administrated orally, and thus have the potential to be developed into an oral antitumor drug.

TABLE 3

Growth inhibition of 2-indolinone derivative (Indo 5) in nude mouse orthotopic tumor models inoculated with human hepatoma cells

| Group | Administration route | number of animals Start | number of animals End | Average weight (X ± S) Start | Average weight (X ± S) End | Weight of tumor (g) | Tumor inhibition rate (%) |
|---|---|---|---|---|---|---|---|
| Vehicle control group | — | 9 | 9 | 22.44 ± 1.18 | 22.16 ± 2.61 | 1.062 ± 0.916 | — |
| Intraperitoneal low dose group (18 mg/kg) | Pi. | 9 | 9 | 22.30 ± 0.90 | 20.61 ± 2.33 | 0.473 ± 0.497 | 55.5 |
| Intraperitoneal high dose group (36 mg/kg) | Pi. | 9 | 9 | 22.56 ± 1.29 | 21.18 ± 1.44 | 0.399 ± 0.486 | 62.4 |
| Gavage group (36 mg/kg) | PO. | 9 | 9 | 22.29 ± 1.78 | 21.01 ± 3.41 | 0.401 ± 0.530 | 62.2 |

Experimental Example 5

Ability of 2-Indolone Derivatives of the Present Disclosure to Inhibit the Lung Orthotopic Tumor Formation of Lung Cancer Cell A549

The study was intended to test the ability of 2-indolone derivatives (Indo 5 as an example) of the present disclosure to inhibit the lung orthotopic tumor formation of lung cancer cell A549.

Establishment of animal models: Human lung cancer cell line A549 was cultured in 1640 medium containing 10% fetal bovine serum (supplemented with 100 μl/mL of penicillin and 100 μl/mL of streptomycin) in a cell incubator at 37° C. and containing 5% $CO_2$. The medium was changed once every 1-2 days. Cells were digested with 0.25% trypsin, and centrifuged at 1,000 r/min for 5 minutes. The supernatant was discarded, and fresh medium was added for subculture. The subcultured tumor cells were digested into suspensions under a sterile condition, and orthotopically injected into BALB/c nude mice at the left chest between the third and fourth ribs (3.0×10$^6$ cells/mouse, 30 μl). The inoculation needle entered into the pulmonary lobe at a depth of about 5 mm. The inoculation day is labeled as D0. Seven days later, animals were weighed and randomized into groups based on body weight. At this point, chest X-ray showed that tumor was formed in the lung of the mouse, suggesting that the animal model was established successfully.

Method: Animal models were randomized into three groups, vehicle control group (DMSO injected intraperitoneally), intraperitoneal low dose group (18 mg/kg), and intraperitoneal high dose group (36 mg/kg). The animals received treatment once every 24 hours. After 6 times of successive administration, animals were kept for another 30 days. At the end of this experiment, animals were sacrificed, and dissected to obtain lungs. Tumor was dissected and weighed.

The results were shown in Table 4. As can be seen, 2-indolone derivatives (Indo 5) of the present disclosure may significantly inhibit the lung orthotopic tumor formation of lung cancer cells A549, and showed a dose-dependency.

with 200 μl PBS for 3 times. P-Tyr-100 antibody was diluted at a ratio of 1:1000, added to the 96-well plate, and incubated at room temperature for 60 minutes. The plate was washed with 200 μl PBS for 3 times. Horseradish peroxidase conjugated secondary antibody was diluted and added in an amount of 100 μl to the 96-well plate, and incubated at room temperature for 30 minutes. Then the plate was washed with 200 μl PBS/T for 3 times. 100 μl TMB substrate was added, and incubated at room temperature for 15 minutes. Then 100 μl stop solution was added, and mixed evenly. Absorbance was read at 450 nm using a spectrophotometer. $IC_{50}$ (a concentration of the compound at which the inhibition rate of kinase activity reaches 50%) was calculated with software SPSS.

TABLE 4

Abiltity of 2-indolone derivatives (Indo 5) of the present disclosure to inhibit the lung orthotopic tumor formation of lung cancer cells A549

| Group | Administration route | number of animals | | Average weight (X ± S) | | Weight of tumor (g) | Tumor inhibition rate (%) |
|---|---|---|---|---|---|---|---|
| | | Start | End | Start | End | | |
| Vehicle control group | — | 10 | 8 | 20.7 ± 0.1 | 19.3 ± 0.7 | 0.378 ± 0.13 | — |
| intraperitoneal low dose group (18 mg/kg) | Pi. | 10 | 9 | 20.8 ± 0.1 | 19.5 ± 0.7 | 0.288 ± 0.08 | 23.8 |
| intraperitoneal high dose group (36 mg/kg) | Pi. | 10 | 9 | 20.9 ± 0.2 | 20.4 ± 0.3 | 0.224 ± 0.07 | 40.7 |

Experimental Example 6

Specific Inhibition of 2-Indolone Derivatives (Indo 5) of the Present Disclosure on c-Met and Trk Activity 15 receptor tyrosine kinases including c-Met and TrkA/B kinases were selected to test effect of 2-indolone derivatives (Indo 5 as an example) of the present disclosure on their in vitro phosphorylation, respectively, and the experimental methods were as follows:

1) ELISA and Met kinase assay kits (purchased from Cell Signaling) were used to test inhibition of Indo 5 on c-Met kinase activity in vitro: 1010 μl of 10 mM ATP was added into 1.25 ml of 6 μM substrate peptide, and diluted with water to 2.5 ml, to prepare 2×ATP/substrate mixture ([ATP] =40 μM, [Substrate]=3 μm). An enzyme was taken from −80° C. and immediately placed on ice for thaw. It was centrifuged at 4° C. to allow liquid to be concentrated at the bottom of the tube and was quickly placed back on ice. 10 μl DTT (1.25 M) was added to 4×HTScan tyrosine kinase solution (240 mM HEPES pH 7.5, 20 mM MgCl2, 20 mM MnCl2, 12 μM Na3VO4) to prepare DTT/kinase solution. 1.2 ml DTT/kinase solution was added to the tube of each kinase to prepare 4× reaction mixture ([enzyme]=4 ng/μL in 4× reaction cocktail). 12.5 μl 4× reaction mixture and 12.5 μl pre-dissolved Indo 5 (different doses) were incubated at room temperature for 5 minutes, to which 25 μl 2×ATP/ substrate was added, mixed evenly, and then incubated at room temperature for another 30 minutes. 50 μl stop buffer (50 mM EDTA, pH 8) was added to terminate the reaction. 25 μl of the above reactants and 75 μl water were added into a streptavidin-conjugated 96-well plate and incubated at room temperature for 60 minutes. The plate was washed 2) Activity of the rest 14 receptor tyrosine kinases was tested by using Kinase Glo Plus assay format, Progmag, and $IC_{50}$ with regard to kinase activity was calculated based on the inhibition rate.

Results were shown in Table 5. $IC_{50}$ with regard to inhibition of 2-indolone derivatives (Indo 5) of the present disclosure on c-Met kinase was 0.16 μM, $IC_{50}$ for TrkA kinase was 0.022 μM, and $IC_{50}$ for TrkB kinase was 0.23 μM, whereas IC50 for inhibition on other kinases were over 10 μM. These results suggested that 2-indolone derivatives (Indo 5) of the present disclosure significantly inhibited the activity of c-Met and Trk (including TrkA and TrkB) kinases, and exhibited a good selectivity. The results indicated that 2-indolone derivatives (Indo 5) of the present disclosure may specifically inhibit the activity of c-Met and Trk kinases, while have no significant effect on other kinases.

TABLE 5

Specific inhibition of 2-indolone derivatives (Indo 5) of the present disclosure on activities of c-Met and Trk kinases

| Kinase | IC50 (μM) |
|---|---|
| TrkA | 0.022 |
| TrkB | 0.23 |
| c-Met | 0.16 |
| PDGFR | >10 |
| FGFR | >10 |
| AXL | >10 |
| FLT1 | >10 |
| EPHA1 | >10 |
| IGF1R | >10 |
| EGFR | >10 |
| InsR | >10 |
| c-KIT | >10 |

TABLE 5-continued

Specific inhibition of 2-indolone derivatives (Indo 5) of the
present disclosure on activities of c-Met and Trk kinases

| Kinase | IC50 (μM) |
|---|---|
| Ephb1 | >10 |
| RET | >10 |
| EGFR (T790, L858R) | >10 |

Experimental Example 7

Inhibition of 2-Indolone Derivatives (Indo 5) on c-Met Phosphorylation and Signaling Pathway in Hepatoma Cells As previously reported, c-Met signaling pathway mediated by hepatocyte growth factor (HGF) plays an important role in formation and development of tumors. c-Met kinase is a high affinity receptor for HGF, and has essential function in tissue repair, wound healing, liver regeneration and embryonic development. Studies have shown that abnormal expression of c-Met may directly lead to tumorigenesis. By binding to HGF, c-Met activates downstream signaling pathway, disrupts adhesion between tumor cells, promotes cell movement, and thereby enhances invasion ability and angiogenesis of tumor cells. Abnormal expression of c-Met among patients clinically diagnosed with cancer is closely related to poor prognosis, quick disease progression, high metastasis and short survival. c-Met has been recognized as a target for cancer treatment internationally. The present disclosure used two hepatoma cell lines to test the efficacy of the compounds on c-Met signaling pathway. HepG2 cells highly express c-Met, and HGF stimulation may activate c-Met phosphorylation and its downstream signaling pathways, including activation of ERK, Akt, etc. MHCC97-H cell is a hepatoma cell line which secretes HGF itself, and thus this cell has high and persistent level of c-Met phosphorylation under a normal culture condition.

Inhibition of 2-indolone derivatives (Indo 5 as an example) of the present disclosure on HGF-induced c-Met phosphorylation and signaling pathway was tested by using two hepatoma cell lines, HepG2 and MHCC97-H.

Cell culture: HepG2 cells which highly express c-Met and MHCC97-H cells which have persistently active c-Met were cultured in 1640 medium containing 10% fetal bovine serum (supplemented with 100 μl/mL of penicillin and 100 μl/mL of streptomycin) in a cell incubator at 37° C. and containing 5% $CO_2$. The medium was changed once every 1-2 days. Cells were digested with 0.25% trypsin, and centrifuged at 1,000 r/min for 5 minutes. The supernatant was discarded, and fresh medium was added for subculture.

Western Blot Assay:

(A) For HepG2 cells: HepG2 cells were cultured under a serum-free condition for 24 hours and then pre-incubated with various concentrations (0.1 μM, 0.5 μM, 1.0 μM, and 2.0 μM) of Indo 5 or solvent DMSO (0) for 2 h. Then 20 ng/mL HGF (if not added, marked as "-") was added and kept for 5 min. After cell lysis, total protein was extracted. Western blot assay was carried out with c-Met phosphorylated and non-phosphorylated antibodies, ERK phosphorylated and non-phosphorylated antibodies, Akt phosphorylated and non-phosphorylated antibodies (all purchased from Cell Signaling), and GAPDH antibody (purchased from Santa Cruz).

(B) For MHCC97-H cells: MHCC97-H cells were cultured under a normal condition for 24 hours, and then treated with various concentrations (0.1 μM, 0.5 μM, 1.0 μM, and 2.0 μM) of Indo 5 or solvent DMSO (0) or 1 μM SU11274. SU11274 (purchased from Sigma) is a specific c-Met kinase inhibitor which may block activation of c-Met. However, due to solubility and large adverse effect of this compound, it is not an appropriate clinical drug, but may be used as a positive control in this study. After incubation with the compounds for 2 h, the cells were harvested and total protein was extracted. Western blot assay was carried out with c-Met phosphorylated and non-phosphorylated antibodies, ERK phosphorylated and non-phosphorylated antibodies, Akt phosphorylated and non-phosphorylated antibodies (all purchased from Cell Signaling), and GAPDH antibody (purchased from Santa Cruz).

Figure 6A:
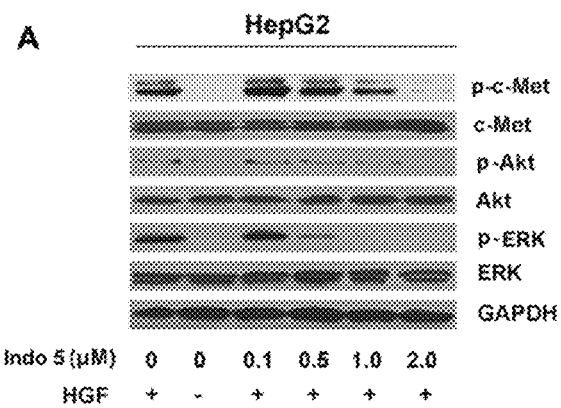
FIG. 6A shows the inhibition of 2-indolone derivative Indo 5 on HGF-induced c-Met phosphorylation and signaling pathway in hepatoma cell line HepG2.
Figure 6B:
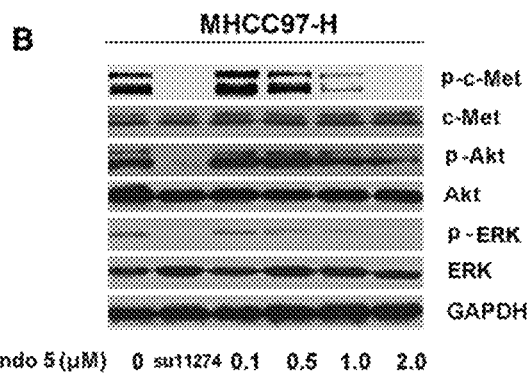
FIG. 6B shows the inhibition of 2-indolone derivative Indo 5 on c-Met phosphorylation and signaling pathway in hepatoma cell line MHCC97-H.

Results were shown in FIGS. 6A and 6B. In HepG2 cells, HGF rapidly induced phosphorylation of c-Met, and Indo 5 inhibited HGF-induced phosphorylation of c-Met in a dose-dependent manner. At 2 μM, c-Met phosphorylation was almost completely inhibited, and the phosphorylation of Akt and ERK which are critical downstream signaling molecules of c-Met were also inhibited (see FIG. 6A). MHCC97-H cell is a highly metastatic human hepatoma cell line. It may secrete HGF, and activate HGF/c-Met signaling pathway through autocrine. Under a normal culture condition, MHCC97-H cells have a high level of c-Met phosphorylation. Indo 5 may inhibit phosphorylation of c-Met and phosphorylation of its downstream signaling pathway molecules Akt and ERK in a dose-dependent manner (see FIG. 6B). At a concentration of 2 μM, the inhibitory effect of Indo 5 was comparable to the positive control SU11274. Results above indicated that 2-indolone derivatives (Indo 5) of the present disclosure significantly inhibited activation of c-Met and phosphorylation of its downstream signaling molecule ERK in a dose-dependent manner, suggesting that it may effectively inhibit HGF/c-Met in in vitro cells, and may be developed into a therapeutic drug for treating tumors with abnormal activation of c-Met and liver cancer.

Experimental Example 8

Inhibition of Indo 5 on TrkA and TrkB Phosphorylation and Signaling Pathways

Trk (NTRK) kinase belongs to a sub-family of the receptor tyrosine kinase family. This sub-family of kinases are neurotrophin receptors, and play an important role in the development and maintenance of the central and peripheral nervous system. Its members include TrkA (NTRK1), TrkB (NTRK2), and TrkC (NTRK3). Trk is closely associated with formation and development of tumors, and inhibiting Trk signaling pathway has already become one of the strategies for tumor treatment. Small molecule inhibitors and therapeutic monoclonal antibodies targeting Trk have been used in clinical intervention to peripheral pain and treatment to central nervous system abnormality and cancer. TrkA is a high affinity receptor for NGF, and TrkB is a high affinity receptor for BDNF. By detecting phosphorylation of TrkA, phosphorylation of TrkB and downstream signals, the effect of 2-indolone derivatives (Indo 5 as an example) of the present disclosure on the signaling pathways may be evaluated, and further the inhibition effect on neuroblastoma, breast cancer, and lung cancer, etc. which are associated with this cellular pathway may be predicted.

Method: Neuroblastoma cells SK-N-SH were cultured in 1640 medium containing 10% fetal bovine serum (supplemented with 100 μl/mL of penicillin and 100 μl/mL of streptomycin) in a cell incubator at 37° C. and containing 5% $CO_2$. The medium was changed once every 1-2 days. The cells were digested with 0.25% trypsin, and centrifuged at 1000 r/min for 5 minutes. The supernatant was discarded, and fresh medium was added for subculture. After culture of SK-N-SH cells under a serum-free condition for 24 hours, various concentrations (0.05 μM, 0.1 μM, 0.5 μM, and 1.0 μM) of Indo 5 or solvent DMSO (0) were added for pre-incubation for 2 h. 500 ng/mL NGF or 200 ng/ml BDNF (if not added, marked as "-") were added to stimulate the cells for 5 min. After cell lysis, total protein was extracted. Western blot assay was carried out with TrkA phosphorylated and non-phosphorylated (p-TrkA) antibodies, TrkB phosphorylated and non-phosphorylated (p-TrkB) antibodies, ERK phosphorylated and non-phosphorylated (p-ERK) antibodies, Akt phosphorylated and non-phosphorylated (p-Akt) antibodies, and GAPDH antibody.

Figure 7:
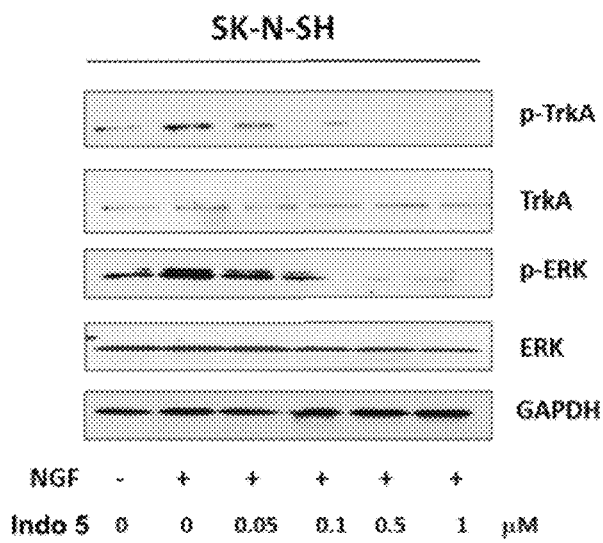
FIG. 7 shows the inhibition of 2-indolone derivative Indo 5 on NGF-induced TrkA phosphorylation and signaling pathway in SK-N-SH cells.
Figure 8:
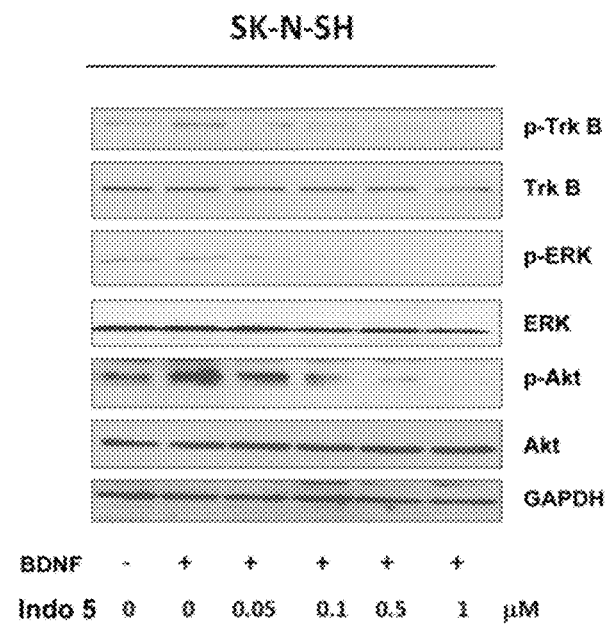
FIG. 8 shows the inhibition of 2-indolone derivative Indo 5 on BDNF-induced TrkB phosphorylation and signaling pathway in SK-N-SH cells.

Results were shown in FIG. 7. 2-indolone derivative (Indo 5) of the present disclosure significantly inhibited phosphorylation of TrkA and phosphorylation of its downstream signaling molecule ERK in a dose-dependent manner. As shown in FIG. 8, 2-indolone derivatives (Indo 5) of the present disclosure significantly inhibited phosphorylation of TrkB and phosphorylation of its downstream signaling molecules including ERK and Akt in a dose-dependent manner. These data suggested that 2-indolone derivatives (Indo 5) of the present disclosure may effectively inhibit Trk signaling pathway in in vitro cells, and may be developed into a therapeutic drug for treating neuroblastoma, breast cancer, and lung cancer, etc.

Experimental Example 9

Inhibition of Indo 5 on Growth of Neuroblastoma SK-N-SH Cells In Vivo

It has been reported that NGF/TrkA plays an important role in formation and development of neurocyte tumors. Tumor-bearing nude mouse models were established with neuroblastoma SK-N-SH cells to observe the effect of 2-indolone derivatives (Indo 5 as an example) of the present disclosure on tumors in the tumor-bearing nude mice.

Model establishment: nu/nu female mice of 6-8 weeks old were fed under an SPF condition in an animal facility for one week, and then each of them was inoculated with $5\times10^6$ neuroblastoma SK-N-SH cells (purchased from ATCC) subcutaneously in left flank. Tumor volume was monitored every day after inoculation. Once the size reached ~100 $mm^3$, mice were divided into groups. Each nude mouse was numbered, and the tumor size was measured. The measured data was entered into EXCEL for sorting and thus excluding extreme values. Random numbers were generated corresponding to the number of the mice, and the mice were randomly grouped using these random numbers.

Method: Intraperitoneal injection groups, at doses of 4 mg/kg, 8 mg/kg, and 16 mg/kg, respectively; gavage group (16 mg/kg); and vehicle control group, injected with the same volume of DMSO. Each group included 10 animals. The mice received treatment once every 24 h, and a total of 6 times of administrations were given. During administration, changes of tumor size (length×width×width/2) were monitored and recorded in a real-time manner, and the results were expressed as mean±standard deviation. Two weeks later, mice were sacrificed, the visible tumors were isolated and weighed, and the inhibition rate of the compounds on tumors was calculated.

Figure 9:
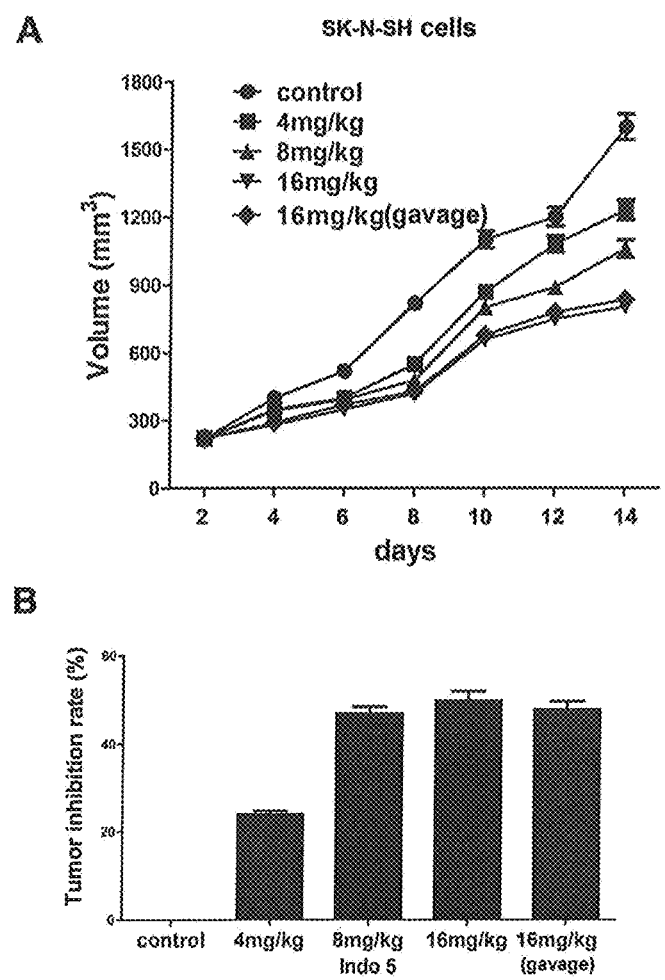
FIG. 9 shows the inhibitory effect of 2-indolone derivative Indo 5 via intraperitoneal injection and gavage administration on tumor in SK-N-SH tumor-bearing mice.

FIG. 9 showed inhibition of compound Indo5 at different doses on SK-N-SH tumor-bearing mice; A represents the tumor volume change curve, and B represents the inhibition rate. It showed that intraperitoneal injection of the compound Indo 5 may effectively inhibit growth of SK-N-SH cells and exhibited a dose-dependency. The tumor inhibition rate was calculated from the measured data, and the calculated result showed that the compound Indo 5 via intraperitoneal administration may inhibit growth of tumor cells in a dose-dependent manner. The inhibition rate of the highest dose (16 mg/kg) of compound Indo 5 on in vivo proliferation of SK-N-SH cells was 50%, indicating that the compound Indo 5 has significant anti-tumor effect on nude mouse models subcutaneously inoculated with SK-N-SH tumor cells.

In addition, the effect of gavage and intraperitoneal administrations on in vivo proliferation of SK-N-SH cells were compared, and the result showed that the inhibition rate of gavage administration at 16 mg/kg on proliferation of tumor cells was 48%, which was comparable to that of intraperitoneal injection, suggesting that the compounds of the present disclosure has anti-tumor effect when orally administered and has the potential to be developed into oral anti-tumor drugs.

INDUSTRIAL APPLICABILITY

The present disclosure provides 2-indolone derivatives and preparation method thereof, and these substances have tyrosine kinase inhibitory activity, and may be used as active ingredients for tyrosine kinase inhibitor drugs or anti-tumor drugs, and thus may be used for the prevention and treatment of tumor diseases and the development of anti-tumor drugs.

What is claimed is:

1. A compound having tyrosine kinase inhibitory activity, which is a compound of formula I, geometric isomers or pharmaceutically acceptable salts thereof:

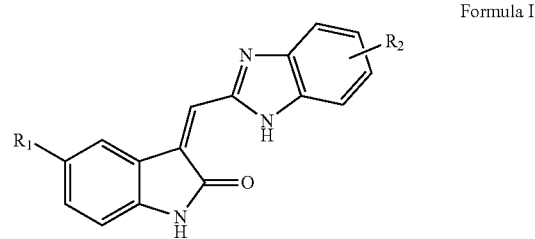

Formula I wherein $R_2$ is hydrogen or halogen; $R_1$ is $SO_2NR_3R_4$, in which $R_3$ is hydrogen or methyl, $R_4$ is phenyl, cyclohexyl, halogen-substituted phenyl, methylphenyl, ethylphenyl, ethoxyphenyl, hydroxyphenyl or β-naphthyl.

2. The compound according to claim 1, wherein the compound of formula I is any one of the following:
3-(1H-benzimidazol-2-methylene)-5-(β-naphthylaminosulfo)-2-indolone (Indo 1);
3-(1H-benzimidazol-2-methylene)-5-(3-chloro-4-fluorophenylaminosulfo)-2-indolone (Indo 2);
3-(1H-benzimidazol-2-methylene)-5-(N-methylphenylaminosulfo)-2-indolone (Indo 3);
3-(1H-benzimidazol-2-methylene)-5-(cyclohexylaminosulfo)-2-indolone (Indo 4);
3-(1H-benzimidazol-2-methylene)-5-(2-methylphenylaminosulfo)-2-indolone (Indo 5);

3-(1H-benzimidazol-2-methylene)-5-(4-chlorophenylaminosulfo)-2-indolone (Indo 6);
3-(1H-benzimidazol-2-methylene)-5-(4-hydroxyethylphenylaminosulfo)-2-indolone (Indo 7);
3-(1H-benzimidazol-2-methylene)-5-(4-methylphenylaminosulfo)-2-indolone (Indo 8); or
3-(1H-benzimidazol-2-methylene)-5-(4-ethoxyphenylaminosulfo)-2-indolone (Indo 9).

3. A preparation method of the compound according to claim 1, comprising:
mixing a compound of formula II and a compound of formula III in methanol, ethanol or isopropanol, or a mixed solution thereof,

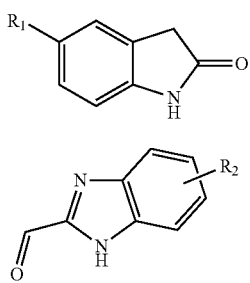

Formula II

Formula III adding thereto a basic or acidic catalyst, and refluxing to obtain the desired product, wherein $R_1$ and $R_2$ are defined as claim 1.

4. The preparation method according to claim 3, wherein during the preparation, the basic catalyst is selected from inorganic basic compounds, including potassium hydroxide, sodium hydroxide, ammonia, calcium oxide and aqueous solution thereof; and organic amines, including triethylamine, piperidine, dimethylaminopyridine, 2,4,5-trimethylpyridine or pyridine; and the acidic catalyst is selected from inorganic acids, including hydrochloric acid and phosphoric acid; and organic acids, including p-toluenesulfonic acid and acetic acid.

5. A composition, which is a pharmaceutical composition comprising one or more of the compounds having tyrosine kinase inhibitory activity according to claim 1 and pharmaceutically acceptable carriers or excipients.

6. A method of inhibiting a tyrosine kinase or treating a tumor wherein the tumor is selected from the group consisting of breast cancer, lung cancer, liver cancer, gastric cancer, skin cancer, neuroblastoma and leukemia, comprising administering an effective amount of the compound, geometric isomers or pharmaceutically acceptable salts thereof according to claim 1 to a subject in need thereof.

7. The method according to claim 6, wherein the compound is 3-(1H-benzimidazol-2-methylene)-5-(2-methylphenylaminosulfo)-2-indolone (Indo 5).

8. The method according to claim 6, wherein the compound is 3-(1H-benzimidazol-2-methylene)-5-(2-methylphenylaminosulfo)-2-indolone (Indo 5), and the tumor is liver cancer, lung cancer or neuroblastoma.

* * * * *